United States Patent [19]

Clader et al.

[11] Patent Number: 5,326,762

[45] Date of Patent: Jul. 5, 1994

[54] INHIBITORS OF ACYL-COENZYME A: CHOLESTEROL ACYL TRANSFERASE

[75] Inventors: John Clader, Cranford; Sundeep Dugar, Parlin, both of N.J.; Timothy Kogan, Half Moon Bay, Calif.; Bradley Tait, Canton, Mich.; Wayne Vaccaro, Princeton, N.J.

[73] Assignee: Schering Corporation, Kenilworth, N.J.

[21] Appl. No.: 885,420

[22] Filed: May 19, 1992

Related U.S. Application Data

[62] Division of Ser. No. 547,644, Jul. 3, 1990, Pat. No. 5,149,709.

[51] Int. Cl.$^5$ .................... H01N 43/40; C07D 211/70
[52] U.S. Cl. ........................... 514/241; 514/245;
514/255; 514/269; 514/345; 514/346; 514/351;
514/352; 514/354; 514/355; 514/357; 514/398;
514/399; 514/400; 514/824; 544/211; 544/215;
544/216; 544/298; 544/322; 544/334; 544/335;
544/382; 544/383; 544/384; 544/387; 544/390;
544/391; 544/396; 544/398; 544/399; 544/400;
544/401; 544/402; 548/338.1; 548/334.1;
548/110; 548/324.1; 546/290; 546/292;
546/304; 546/307; 546/312; 546/314; 546/337
[58] Field of Search ............... 546/337, 290, 292, 304,
546/307, 312, 314; 544/311, 215, 216, 298, 322,
334, 335, 382, 383, 384, 387, 390, 391, 396, 398,
399, 400, 401, 402; 548/341, 337; 514/241, 245,
255, 769, 345, 346, 351, 352, 354, 355, 357, 398,
399, 400, 824

[56] References Cited

U.S. PATENT DOCUMENTS

| | | | |
|---|---|---|---|
| 3,784,577 | 1/1974 | Fukurmaru et al. | 260/404 |
| 4,420,475 | 12/1983 | Damon et al. | 424/184 |
| 4,434,161 | 2/1984 | Barcza | 424/184 |
| 4,456,619 | 6/1984 | Kathawala | 424/324 |
| 4,518,789 | 5/1985 | Yu et al. | 560/105 |
| 4,603,145 | 7/1986 | DeVries et al. | 514/539 |
| 4,716,175 | 12/1987 | Hoefle et al. | 546/337 |
| 4,758,573 | 7/1988 | Manley et al. | 546/337 |
| 4,968,721 | 11/1990 | Martin et al. | 514/649 |

FOREIGN PATENT DOCUMENTS 25569 3/1981 European Pat. Off. .

OTHER PUBLICATIONS

Chemical Abstracts, vol. 62, No. 5223h, Mollor et al., 1965 "Addition of derivatives under catalytic action of anhydrous aluminum chloride."

*Primary Examiner*—C. Warren Ivy
*Assistant Examiner*—Raymond Covington
*Attorney, Agent, or Firm*—Paul A. Thompson; Anita W. Magatti

[57] ABSTRACT

Amides of the formula

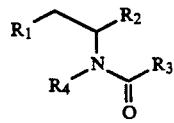

wherein $R_1$ and $R_2$ are independently heteroaryl, X-substituted heteroaryl, X-substituted phenyl, N-substituted triazinyl or N-substituted imidazolyl; and in addition, one of $R_1$ and $R_2$ can be as defined above and the other can be phenyl;

$R_3$ is an alkyl chain of 2 to 25 carbon atoms, saturated or unsaturated; an alkyl chain as defined substituted by one or more substituents selected from the group consisting of phenyl, X-substituted phenyl, heteroaryl and X-substituted heteroaryl; an alkyl chain as defined interrupted by one or more groups independently selected from the group consisting of —O—, —S—, —SO—, —SO$_2$—, —NH—, —N(lower alkyl)—, —C(O)—, phenylene, X-substituted phenylene, heteroarylene and X-substituted heteroarylene; or an interrupted alkyl chain as defined substituted by one or more substituents selected form the group consisting of phenyl, X-substituted phenyl, heteroaryl and X-substituted heteroaryl;

$R_4$ is hydrogen, lower alkyl, phenyl, X-substituted phenyl, heteroaryl or X-substituted heteroaryl; or a pharmaceutically acceptable salt thereof, useful as inhibitors of acyl-coenzyme A:cholesterol acyl transferase and therefore in the treatment of atherosclerosis are disclosed.

10 Claims, No Drawings

INHIBITORS OF ACYL-COENZYME A: CHOLESTEROL ACYL TRANSFERASE

This is a division of application Ser. No. 07/547,644, filed Jul. 3, 1990 now U.S. Pat. No. 5,149,109.

BACKGROUND OF THE INVENTION

The present invention relates to 1,2-disubstituted ethyl amides useful in the treatment and prevention of atherosclerosis.

Atherosclerotic coronary heart disease represents the major cause for death and cardiovascular morbidity in the western world. Risk factors for atherosclerotic coronary heart disease include hypertension, diabetes mellitus, family history, male sex, cigarette smoking and serum cholesterol. A total cholesterol level in excess of 225–250 mg/dl is associated with significant elevation of risk.

Cholesterol esters are a major component of atherosclerotic lesions and the major storage form of cholesterol in arterial wall cells. Formation of cholesterol esters is also a key step in the intestinal absorption of dietary cholesterol. The intracellular esterification of cholesterol is catalyzed by the enzyme acyl CoA:- cholesterol acyl transferase (ACAT, EC 2.3.1.26). Thus, inhibition of ACAT is likely to inhibit the progression of atherosclerotic lesion formation, decrease the accumulation of cholesterol esters in the arterial wall, and block the intestinal absorption of dietary cholesterol.

A number of amides have been reported as being useful in lowering cholesterol and/or in inhibiting the formation of cholesterol-containing lesions in mammalian arterial walls. U.S. Pat. No. 3,784,577 to Fukurmaru et al discloses fatty acid amide derivatives of the formula R-CONHR$^1$ wherein RCO is a fatty acid radical and R$^1$ is 1-α-benzylbenzyl.

U.S. Pat. No. 4,603,145 to De Vries et al discloses diaryl alkanamides of the formula

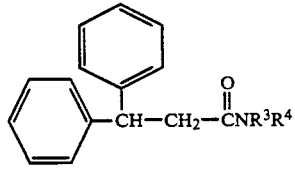

wherein R$^3$ and R$^4$ independently include benzyl and phenethyl.

U.S. Pat. No. 4,420,475 to Damon et al discloses silicon-bearing amides of the formula

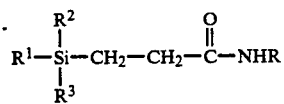

wherein R$^1$, R$^2$ and R$^3$ independently can be alkyl, phenyl, benzyl or phenethyl and R can be 1-α-benzylbenzyl optionally substituted in the phenyl rings. U.S. Pat. No. 4,434,161 to Barcza discloses similar compounds having a sulfur atom in the chain between the silicon atom and the carbonyl group.

U.S. Pat. No. 4,456,619 to Kathawala discloses amides of 2-alkynoic acids of the formula

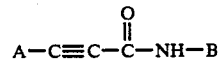

wherein A is alkyl, alkenyl or cyclopropanyl-substituted alkyl and B can be 1-α-benzylbenzyl, optionally substituted in the phenyl rings.

U.S. Pat. No. 4,716,175 to Hoefle et al discloses fatty acid amides of the formula

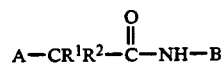

wherein A is an alkyl chain, R$^1$ and R$^2$ can each be phenylmethyl, and B can be phenyl, benzyl, pyrimidinyl or pyridyl.

U.S. Pat. No. 4,518,789 to Yu et al discloses dermatologically useful phenyl alpha-acyloxyacetamides of the formula

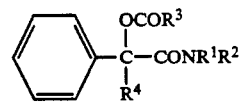

wherein R$^1$ and R$^2$ can be hydrogen, alkyl or aralkyl and R$^3$ and R$^4$ can be hydrogen, alkyl, aralkyl or aryl.

While some of these diphenylethylamides have shown in vitro ACAT inhibitory activity, none have been reported to show significant activity in whole animal models of atherosclerosis.

SUMMARY OF THE INVENTION

Novel compounds of the present invention which show significant in vivo atherosclerotic activity are represented by the formula

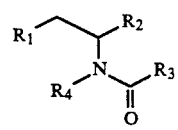

wherein R$_1$ and R$_2$ are independently a heteroaryl group selected from the group consisting of pyridinyl, pyrimidinyl, pyrazinyl, quinolyl, triazinyl, imidazolyl, thiophenyl, oxazolyl and furanyl; X-substituted heteroaryl wherein X is 1 to 3 substituents independently selected from the group consisting of halogeno, lower alkyl, hydroxy, lower alkoxy, amino, lower alkylamino, lower dialkylamino, acetamido, methanesulfonylamino, 2-(trimethylsilyl)ethoxymethyl, carboxy and lower alkoxycarbonyl; X-substituted phenyl; or N-substituted triazinyl or N-substituted imidazolyl wherein the N-substituents are selected from the group consisting of lower alkyl, 2-(trimethylsilyl)ethoxymethyl and R$_5$CO— wherein R is lower alkyl, phenyl, benzyl or 2,2-dimethylpropyl;

and in addition, one of R$_1$ and R$_2$ can be as defined above and the other can be phenyl;

R$_3$ is an alkyl chain of 1 to 25 carbon atoms, branched or straight, saturated or containing one or more double bonds; an alkyl chain as defined substituted by one or more substituents selected from the group consisting of phenyl, X-substituted phenyl, heteroaryl and X-substituted heteroaryl; an alkyl chain as defined interrupted by one or more groups independently selected from the group consisting of —O—, —S—, —SO—, —SO$_2$—, —NH—, —N(lower alkyl)—, —C(O)—, phenylene, X-substituted phenylene, heteroarylene and X-substituted heteroarylene; or an interrupted alkyl chain as defined substituted by one or more substituents selected from the group consisting of phenyl, X-substituted phenylene, heteroarylene and X-substituted heteroarylene; or an interrupted alkyl chain as defined substituted by one or more substituents selected from the group consisting of phenyl, X-substituted phenyl, heteroaryl and X-substituted heteroaryl;

$R_4$ is hydrogen, lower alkyl, phenyl, X-substituted phenyl, heteroaryl or X-substituted heteroaryl; or a pharmaceutically acceptable salt thereof.

Preferred are compounds of formula I wherein $R_1$ is amino-substituted phenyl and $R_2$ is phenyl.

Another group of preferred compounds is that wherein one of $R_1$ and $R_2$ is lower alkoxy-substituted phenyl and the other is phenyl, or each of $R_1$ and $R_2$ is lower alkoxy-substituted phenyl, preferably wherein lower alkoxy is methoxy.

Also preferred are compounds wherein one of $R_1$ and $R_2$ is hydroxy-substituted phenyl and the other is phenyl, or each of $R_1$ and $R_2$ is hydroxy-substituted phenyl.

Still another group of preferred compounds is that wherein one of $R_1$ and $R_2$ is a hetereroaryl group and the other is phenyl. Preferred hetereroaryl groups are pyridyl, quinolyl and imidazolyl.

Yet another group of preferred compounds is that wherein one of $R_1$ and $R_2$ is carboxy-substituted phenyl or lower alkoxycarbonyl-substituted phenyl and the other is phenyl.

Also preferred are compounds of formula I wherein $R_3$ is a diphenyl-substituted alkyl chain, especially diphenylmethyl or diphenylethyl (i.e. —C(O)$R_3$ is diphenylacetyl or 2,3-diphenylpropanoyl), or CH$_3$(CH$_2$)$_7$CH=CH(CH$_2$)$_7$— (i.e. —C(O)$R_3$ is oleoyl). A preferred substituent for $R_4$ is hydrogen.

Especially preferred are compounds of formula I wherein $R_1$ is amino-substituted phenyl, $R_2$ is phenyl, $R_3$ is diphenylmethyl or CH$_3$(CH$_2$)$_7$CH=CH(CH$_2$)$_7$— and $R_4$ is hydrogen.

This invention also relates to the use of the ACAT inhibitors of the present invention as hypolipidemic and hypocholesterolemic agents in mammals.

In another aspect, the invention relates to pharmaceutical compositions comprising an ACAT inhibitor of the present invention in a pharmaceutically acceptable carrier.

DETAILED DESCRIPTION

As used herein, the term "lower alkyl" means straight or branched alkyl chains of 1 to 6 carbon atoms and "lower alkyoxy" similarly refers to alkoxy groups having 1 to 6 carbon atoms.

Halogeno refers to fluorine, chlorine, bromine or iodine radicals.

"Phenylene" means a bivalent phenyl group, including ortho, meta and para-substitution and "heteroarylene" similarly means a bivalent heteroaryl group.

Where $R_1$ or $R_2$ is a heteroaryl group containing a secondary amino group (e.g. triazinyl or imidazolyl), the $R_1$ or $R_2$ heteroaryl group can be attached to the rest of the molecule either by a ring carbon or by the secondary amino group (e.g. 1-imidazolyl or 2-imidazolyl). Also, if it is not the point at which the ring is attached to the molecule, the secondary amino group can be substituted with a substituent selected from the group consisting of lower alkyl, 2-(trimethylsilyl)ethoxymethyl, and $R_5$CO—, wherein $R_5$ is lower alkyl, phenyl, benzyl or 2,2-dimethylpropyl.

The alkyl chain as defined in $R_3$ can be a radical of a synthetic or natural fatty acid, either saturated or containing one or more carbon to carbon double bonds, or can be an interrupted alkyl chain wherein one or more of the carbon atoms in the chain can be replaced by an —O—, —S—, —SO—, —SO$_2$—, —NH—, —N(lower alkyl)—, —C(O)—, phenylene or heteroarylene group. When substituted by optionally substituted phenyl or heteroaryl groups, the alkyl chain or interrupted alkyl chain may be independently substituted on different carbon atoms, di-substituted on one carbon atom, or both.

One skilled in the art will recognize that the number of double bonds present, the replacement of carbon atoms in the chain and the presence of substitutents on the carbon atoms in the chain are all dependent on the length of the chain: shorter alkyl chains cannot accommodate as many bonds, carbon replacements or substituents as longer alkyl chains. In general, unsaturated alkyl chains contain 1 to 4 double bonds, conjugated or non-conjugated. Where carbon atoms are replaced, 1 to 4 replacement groups can be present. Similarly, when carbon atoms in the chain are substituted, 1 to 4 substituents can be present.

Examples of alkyl chains are as follows, wherein the group —C(O)$R_3$ is named: palmitoyl, 2,2-dimethylpalmitoyl, caproyl, capryloyl, stearoyl, dodecanoyl, and 2,2-dimethyldodecanoyl.

Examples of unsaturated —C(O)$R_3$ groups are oleoyl, 2,2-dimethyloleoyl, linoleoyl, linolenoyl, elaidoyl, eicosatetraenoyl, and eicosapentaenoyl.

Examples of —C(O)$R_3$ groups wherein the carbon atoms are substituted are phenylacetyl and those having the formula —C(O)CH(C$_6$H$_4$X)—(CH$_2$)$_n$—C$_6$H$_4$X wherein X is hydrogen or is as defined above and n is 0 to 10, for example diphenylacetyl, 2,2-diphenylpropanyl, and di-(4-chlorophenyl)acetyl or 2,3-diphenylpropanyl.

Examples of —C(O)$R_3$ groups wherein carbon atoms in the chain are replaced are: 3-methoxy-4-(tetradecyloxy)-benzoyl, 11-[N-(2,2-diphenylacetyl)amino]undecanoyl and phenoxyundecanoyl.

Compounds of the invention have at least one asymmetrical carbon atom and therefore include rotational isomers. The invention includes d and l isomers in both pure form and in admixture, including racemic mixtures. Isomers can be prepared using conventional techniques, either by reacting enantiomeric starting materials or by separating isomers of a compound of formula I.

Isomers may include geometric isomers, e.g. when $R_3$ contains a double bond. All such isomers are contemplated for this invention.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared under standard reaction conditions well known in the art. For example, a carboxylic acid of formula II can be converted to the acid chloride by treatment with thionyl or oxalyl chloride in a solvent such as dichloromethane, then reacted with an amine of formula III in the presence of a tertiary amine base such as triethylamine, 4-dimethylaminopyridine (DMAP) or N-methylmorpholine (NMM):

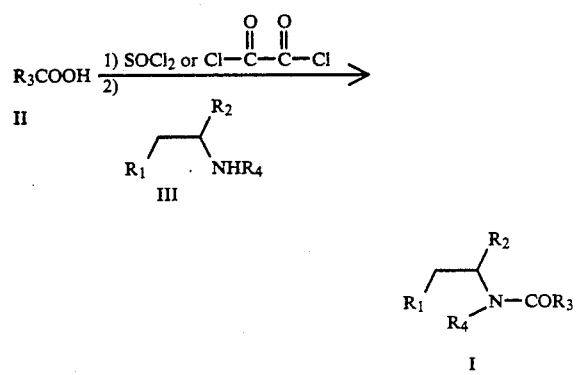

Alternatively, the acid of formula II and amine of formula III can be reacted in the presence of a coupling agent such as dicyclohexylcarbodiimide (DCC) or 1-(3-dimethylaminopropyl)-3-ethylcarbodiimide (EDCI) and a base such as triethylamine, DMAP or NMM in a solvent such as dichloromethane or THF at a temperature of 0° to 23° C. In a third method, the carboxy group of acid II can be activated via the intermediacy of an active ester such as that derived from 1-hydroxybenzotriazole (HOBT).

Starting carboxylic acids of formula II are commercially available or can be prepared by well known methods.

Amines of formula III can be prepared by several methods. In one method, an aldehyde of formula IV, either commercially available or easily prepared by methods known in the art, is reacted with triethylphosphite and benzylcarbamate to obtain a phosphorane of formula V. The phosphorane is then reacted with a second aldehyde of of formula VI to obtain an enamine of formula VII. The enamine is reduced to the desired amine by reaction with hydrogen gas at 50 psi in the presence of a suitable catalyst such as 10% palladium on carbon. The reaction scheme is shown below:

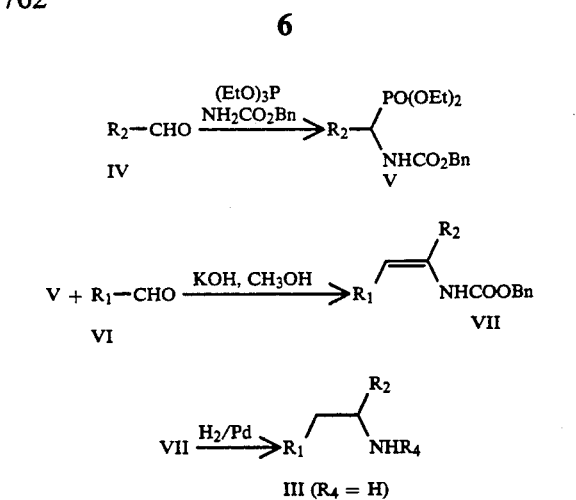

In a second method for preparing an amine of formula III, an aldehyde of formula IV is converted to an N-trimethylsilylimine of formula VIII by reaction with lithium hexamethyldisilazide. The compound of formula VIII is then treated with a lithium reagent of formula IX to obtain the amine of formula III. The reaction scheme is as follows:

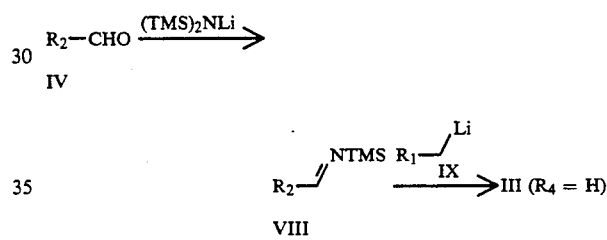

A third method for preparing amines of formula III comprises reaction of a ketone of formula X with an amine of the formula $NH_2X$, wherein X is hydroxy or $R_4$ as defined above, to obtain the corresponding imine of formula XI. The imine is reduced to the desired amine, for example by reaction with hydrogen gas at 50 psi in the presence of a suitable catalyst such as 10% palladium on carbon or by reaction with zinc metal in a solvent such as acetic acid. The reaction scheme is shown as follows:

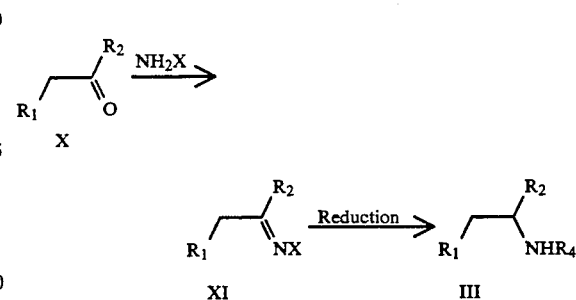

The ketone of formula X may be prepared by several methods. For ketones of formula Xa wherein $R_2$ is phenyl or substituted phenyl, a carboxylic acid chloride of formula XII can be reacted with a phenyl or substituted phenyl derivative of formula XIII in the presence of a Lewis acid such as aluminum chloride:

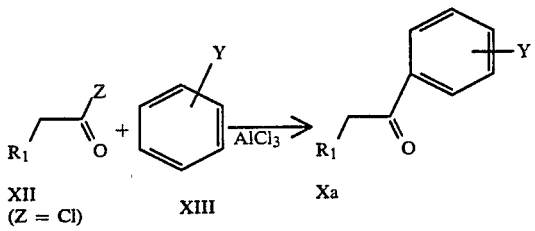

wherein Y are the phenyl substituents as defined in $R_2$ above. Alternatively, compounds wherein $R_2$ is phenyl or substituted phenyl can be prepared by reaction of a carboxylic acid of formula XIIa with a compound XIII in the presence of a strong dehydrating acid such as polyphosphoric acid or phosphorus pentoxide in methanesulfonic acid.:

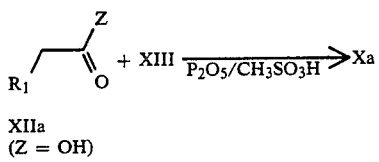

Another method for preparing ketones of formula X comprises reacting a nitrile of formula XIV with a carboxylic acid ester of formula XV in the presence of an alkoxide base such as sodium ethoxide, then hydrolyzing and decarboxylating the product using a strong acid such as 48% hydrobromic acid:

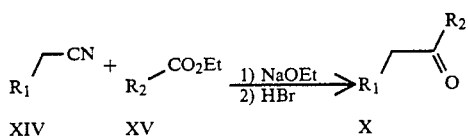

For ketones of Formula Xb wherein $R_1$ is 1-imidazolyl, imidazole can be reacted with a bromoketone of formula XVI:

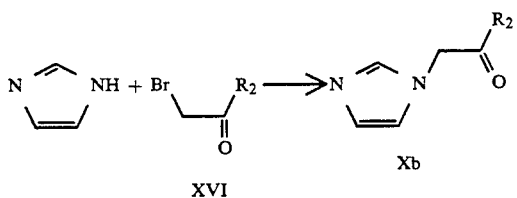

Reactive groups not involved in the above processes can be protected during the reactions with conventional protecting groups which can be removed by standard procedures after the reaction. The following table shows some typical protecting groups:

| Group to be protected | Protected group |
| --- | --- |
| —COOH | —COOalkyl, —COObenzyl, —COOphneyl |
| \>NH | \>NCOalkyl, \>NCOObenzyl, |
| | \>NCOphenyl, |
| | \>NCH₂OCH₂CH₂Si(CH₃)₃, |
| | \>NC(O)CH₂C(CH₃)₃ |
| —OH | —OCH₃ |
| —NHQ wherein Q is any amino substituent defined above | —NRCOCH₃ |
| | —NRCH₂—C₆H₅ |
| —NH₂ | —N(succinimide) |

We have found that the compounds of this invention are inhibitors of ACAT in vitro and in whole animal models the compounds have been found to significantly reduce the formation of liver cholesterol esters. Thus, compounds of this invention are hypocholesterolemic and hypolipidemic agents by virtue of their ability to inhibit the esterification and intestinal absorption of cholesterol; they are therefore useful in the treatment and prevention of atheroclerosis in mammals, in particular in humans.

In addition to the compound aspect, the present invention therefore also relates to a method of treating atherosclerosis, in particular by reducing serum cholesterol, which method comprises administering to a mammal in need of such treatment a hypocholsterolemic effective amount of a compound of this invention. The compound is preferably administered in a pharmaceutically acceptable carrier suitable for oral administration.

The in vitro and in vivo activity of the present compounds can be determined by the following procedures.

ACAT Assay (in vitro)

This assay measures the activity of ACAT by measuring the ACAT-mediated transfer of tritiated oleic acid from acyl-CoA to cholesterol to give labelled cholesterol oleate. Rat liver microsomes are used as the source of ACAT. Assays are performed in round bottom microtiterplates using a total incubation volume of 50 μL. Each incubation well receives 10 μL assay buffer (0.5M KHPO₄, 10 μM dithiothreitol, pH 7.4), 7.5 μL of 40 mg/mL BSA (Bovine Serum Albumin) and 12.5 μg of microsomal protein. The test compound (in sufficient amount to bring the final concentration to from 0.1 to 25 μM), reference compound, or vehicle control is added and the final volume brought to 47 μL. The microtiterplate is then floated on the surface of a 37° C. water bath for fifteen minutes. Incubations are started by the addition of 3 μL ³H-acyl CoA (1 μCi/well, final concentration of 10 μM acyl CoA). The plate is then returned to the water bath for 15 minutes. The incubations are then terminated by application of 15 μL from each incubation to individual lanes on a thin layer plate (Silica Gel GF 20×20 cm). Standards are applied to several lanes so that the cholesterol ester band can be identified. After drying, the plates are eluted with 90:10:1 petroleum ether:diethyl ether:acetic acid. The standards are visualized via iodine vapor, and the regions corresponding to cholesterol ester are scraped into 7 mL scintillation vials. 4 mL of scintillant are added to each vial, and the radioactivity quantified. Background count is determined by the boiled controls. Full activity is determined by activity in the presence of vehicle. The percent inhibition is calulated by subtracting the background from both control and test samples, and the test value is calculated as a percentage of the control. For IC$_{50}$ determinations, the inhibition is plotted against drug does on a log scale and the concentration at which 50% inhibition is obtained is determined.

In Vivo Assay of Hypolipidemic Agents Using the Hyperlipidemic Hamster

Hamsters are separated into groups of six and given a control cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by IM injection of ketamine and sacrificed by decaptitation. Blood is collected into vacutainer tubes containing EDTA for plasma lipid analysis and the liver excised for tissue lipid analysis. Data is reported as percent reduction of lipid versus control.

The present invention also relates to a pharmaceutical composition comprising a compound of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic or hypolipidemic dose of a compound of formula I is about 7 to about 30 mg/kg of body weight per day. For an average body weight of 70 kg, the dosage level is therefore from about 500 to about 2000 mg of drug per day, given in a single dose or 2-4 divided doses. The exact dose, however, is determined by the attending clinician and is dependent on the potency of the compound administered, the age, weight, condition and response of the patient.

Following are preparations of starting materials and examples of preparing compounds of formula I.

PREPARATION 1:
1-(4-AMINOPHENYL)-2-PHENYLETHYLAMINE.

Step A: A mixture of 4-nitrobenzaldehyde (5.0 g), triphenylphosphite (8.53 g) and benzylcarbamate (4.16 g) in glacial acetic acid (5 mL) was stirred at 75°-80° C. for 2 hr. The resulting thick solid was dissolved in chloroform (80 mL) and methanol (320 mL) was added; the resulting cloudy solution was refrigerated overnight. The precipitate was collected, washed with cold methanol, and vacuum-dried to give 9.45 grams of crude product. This was crystallized from methanol:-chloroform 4:1 to give 8.28 grams of diphenyl 2-[(4-nitrophenyl)-2-benzyloxycarbonylamino]methylphosphonate.

Step B: A solution of of the above phosphonate (4.0 g) in 50 mL THF was cooled to −40° C. and 10% KOH in methanol (4.3 g) was added dropwise over 30 minutes. The deep-purple solution was stirred for 90 minutes, after which a solution of benzaldehyde (10.89 g) in THF (10 mL) was added in portions while maintaining the reaction temperature at −30° to −40° C. After the addition was complete, the mixture was maintained at −40° C. for 20 minutes, then allowed to come to room temperature. The solvent was removed under vacuum and the residue was extracted into ethyl acetate. The ethyl acetate was then washed with water, aqueous sodium bicarbonate and with brine, dried over magnesium sulfate and evaporated. The residue was chromatographed over silica gel, eluting with 20% ethyl acetate-hexane to give 1.80 of 1-(4-nitrophenyl)-1-benzyloxycarbonylamino-2-phenylethylene.

Step C: A solution of the above product (0.50 g) in ethanol (70 mL) and methanol (40 mL) was hydrogenated at 50 psi over 10% palladium on carbon (0.1 g) for two hours at room temperature. After filtering through celite, the solvent was evaporated to give 0.28 grams of the title compound.

PREPARATION 2:
1-PHENYL-2-[1-[[2-TRIMETHYLSILYL)ETHOXY]-METHYL]-1H-IMIDAZOL-2-YL]ETHYLAMINE

2-Methyl-1-[[(trimethylsily)ethoxy]methyl]imidazole (2.04 g) was dissolved in dry THF (25 mL), cooled to −78° C. and treated with t-butyllithium (5.14 mL). The cooling bath was removed for 10 min., the mixture was recooled to −78° C. and transferred via cannula to a −78° C. solution of N-trimethylsilylbenzaldimine (1.31 mL) (prepared by reaction of benzaldehyde with lithium hexamethyl-disilazide) in THF (25 mL). The reaction was allowed to warm slowly to room temperature overnight (about 18 hr.). The reaction was quenched with sat. ammonium chloride solution and extracted with ethyl acetate (3x). The organic extracts were combined and washed with brine (3x), dried over anhydrous sodium sulfate, filtered through cotton and concentrated in vacuo. The oil was chromatographed on silica, eluting with 5% MeOH/CH$_2$Cl$_2$ followed by 5% NH$_4$OH (conc.)/5% MeOH/CH$_2$Cl$_2$ to provide the title compound as an oil. $^1$H NMR (300 MHz, CDCl$_3$): 7.34 (5H, m, Ar); 7.02 (1H, s, Im-H); 6.92 (1H, s, Im-H); 5.02 (2H, q, J=11 Hz, NCH$_2$O); 4.62 (1H, t, J=6.6 Hz, PhCHNH$_2$); 3.45 (2H, t, J=7.7 Hz, OCH$_2$CH$_2$); 2.64 (2H, Bs, NH$_2$); 0.89 (2H, app t, J=8.2 Hz, CH$_2$CH$_2$Si); −0.02 (9H, s, Si(CH$_3$)$_3$). MS (Cl+/isobutane): 318(M+, 100).

PREPARATION 2A:
2-[1-HEPTYL-1H-IMIDAZOL-2-YL]-1-PHENYLETHYLAMINE

In a manner similar to that described in Preparation 2, treat 2-methyl-1-heptylimidazole to obtain the title compound.

PREPARATION 3: 2-(4-AMINOPHENYL)-1-PHENYLETHYLAMINE

Step A: To a solution of 4-nitrophenylacetic acid (200 g) in benzene (1.5 L) was added oxalyl chloride (200 mL). The mixture was warmed to 50°-60° C. for 2 hrs, after which time benzene and excess oxalyl chloride were distilled off under vacuum at 50° C. until a final volume of 500 mL was achieved. The residue was diluted with benzene (1 L) and cooled to 0° C. To this was added anhydrous aluminum chloride (160 g) portionwise over 15 minutes. Thereafter, the mixture was stirred overnight at room temperature. The reaction mixture was poured over a mixture of ice (3 L) and concentrated HCl (1 L). The resulting slurry was filtered through celite and the precipitate washed with ethyl acetate. The combined filtrates were washed with water, saturated sodium bicarbonate and with brine, dried over sodium sulfate and evaporated to give 227 grams of 2-(4-nitrophenyl)-1-phenylethanone.

Step B: To a solution of the product of Step A (220 g) in pyridine (2.5 L) at 0° C. was added hydroxylamine hydrochloride (70.0 g). The reaction mixture was stirred for 3.5 hours while coming slowly to room temperature. The reaction mixture was poured into water and extracted with dichloromethane. The organic layer was washed with water, dried over sodium sulfate and evaporated. The crude product was filtered through a bed of silica gel, eluting with dichoromethane:hexane 2:1. The solvent was evaporated and the residue was crystallized from ether-hexane to give 160 grams of oxime. This was hydrogenated in two 80-gram lots over 10% Pd/C at 50 psi in ethanol to give, after filtration and evaporation, 128 grams of the title compound.

PREPARATION 4: 1-(4-METHOXYPHENYL)-2-PHENYLETHYLAMINE

Step A: A mixture of methanesulfonic acid (100 g) and $P_2O_5$ (10 g) was stirred at 50°-60° C. until solution was complete, then cooled to room temperature. To this was added phenylacetic acid (2.0 g) and anisole (4.00 g). The mixture was stirred at 50°-60° C. for 90 minutes, cooled to room temperature and poured into ice water (1.2 L). The solution was made basic by gradual addition of solid sodium bicarbonate, then extracted into ethyl acetate (800 mL). The ethyl acetate was dried over magnesium sulfate and evaporated to give 3.88 grams of crude product. This crude product was chromatographed on silica gel eluting with 2% ethyl acetate in hexane, to obtain 2.92 grams of 1-(4-methoxyphenyl)-2-phenylethanone.

Step B: The product of Step A was treated in a manner similar to that described in Preparation 3, Step B, to obtain the title compound.

PREPARATION 5: 1-(4-PYRIDINYL)-2-PHENYLETHYLAMINE

Step A: To a solution of sodium ethoxide (prepared from 2.56, sodium metal) in ethanol (50 mL) was added isonicotinic acid (10.0 g) and phenylacetonitrile (8.54 g) and the mixure was heated at reflux for 2.5 hours. After cooling to room temperature, the mixture was poured into ice water and brought to pH 3 by addition of concentrated HCl. The resulting precipitate was collected, washed with water and dried under vacuum to give 13.6 grams of crude cyanoketone.

A solution of of the above product (5.00 g) was suspended in 48% HBr (30 mL) and the mixture heated at reflux for five hours. After cooling in an ice bath, the mixture was made basic by addition of concentrated ammonia and the mixture was extracted with two 200 mL portions of ethyl acetate. The combined organic layers were washed with water and with brine, dried over magnesium sulfate and evaporated to give 2.71 grams of 1-(4-pyridinyl)-2-phenylethanone.

Step B: The product of Step A was treated in a manner similar to that described in Preparation 3, Step B, to obtain the title compound.

PREPARATION 6: 2-(1-H-IMIDAZOL-1-YL)-1-PHENYLETHYLAMINE

To a solution of imidazole (5.88 g) in THF (100 mL) was added 2-bromoacetophenone (6.84 g). After 1.5 hours, the mixture was transferred to a separatory funnel, washed with saturated sodium bicarbonate, water and with brine, dried over sodium sulfate and evaporated. The residue was passed through a short silica gel column, eluting with 10% methanol in dichloromethane to give 4.51 grams of a yellow solid.

Step B: The product of Step A was treated in a manner similar to that described in Preparation 3, Step B, to obtain the title compound.

PREPARATION 7: RESOLUTION OF 2-(4-AMINOPHENYL)-1-PHENYLETHYLAMINE

Dissolve racemic 2-(4-aminophenyl)-1-phenylethylamine (10.0 g) from Preparation 3 in ethanol (300 mL) with heating and add a solution of di-p-toluoyl-L-tartaric acid (18.2 g) in ethanol (150 mL). Heat the resulting suspension to reflux and add additional ethanol (1 L) until the suspension dissolves. Cool the solution to room temperature, then refrigerate for two days. Filter the resulting precipatate, wash with cold ethanol followed by ethyl acetate and dry under vacuum to give the tartrate salt of 2-(4-aminophenyl)-1-phenuylethylamine. Crystallize again from hot ethanol (725 mL), then convert to the free base by stirring with 1N NaOH solution. Extract the resulting oily suspension with ethyl acetate, wash the ethyl acetate layer with water and with brine, dry over magnesium sulfate and evaporate to obtain a tan solid. Dissolve the solid in dichloromethane and evaporate three times to obtain the pure (−) 2-(4-aminophenyl)-1-phenylethylamine, $[\alpha]_D^{26} = -56.01°$-(MeOH).

The (+) isomer can be similarly prepared by using di-p-toluoyl-D-tartaric acid.

EXAMPLE 1

N-[2-(4-Aminophenyl)-1-Phenylethyl]-2,2-Dimethyl-9-Z-Octadecenamide

To a solution of 2-(4-aminophenyl)-1-phenylethylamine (0.155 g, 0.74 mMol) in THF at 0° C. was added 2,2-dimethyloleoyl chloride (0.2 g, 0.61 mMol) and the reaction mixture was stirred overnight while warming to room temperature. The reaction was quenched by pouring the mixture into water: saturated aqueous sodium bicarbonate (1:1). The resultant solution was extracted into ethyl acetate, the organic layer was dried over magnesium sulfate and evaporated. The residue was purified by chromatography on silica gel, eluting with hexane:ethyl acetate (1:1) to obtain 0.240 mg of the title compound. FAB (M+1)=505. Elemental Analysis: calc. for $C_{34}H_{52}N_2O$ is C=80.9%, H=10.38%, N=5.55%; found C=81.1%, H=10.1%, N=5.43%.

Using a similar procedure, the following compounds can also be prepared:

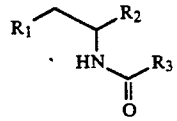

| Compound # | $R_1$ | $R_2$ | $R_3$ | Physical Data |
|---|---|---|---|---|
| 1A | $C_6H_5—$ | $4-HO_2C—C_6H_4—$ | $CH_3(CH_2)_7CH=CH(CH_2)_7—$ | m.p. 102–104° C. |
| 1B | $C_6H_5—$ | $4-HO_2C—C_6H_4—$ | $C_6H_5—CH(C_6H_5)—$ | m.p. 226–228° C. |
| 1C | $4-H_2N—C_6H_4—$ | $C_6H_5—$ | $C_{10}H_{21}C(CH_3)_2—$ | FAB(M + 1) = 423 |
| 1D | $4-H_2N—C_6H_4—$ | $C_6H_5—$ | $\Delta^7\text{-cis-}C_{16}H_{31}—CH(CH_3)—$ | FAB(M + 1) = 491 |
| 1E | $C_6H_5—$ | $4-H_3CO—C_6H_4—$ | $C_{10}H_{21}—C(CH_3)_2—$ | m.p. 110–111° C. |

EXAMPLE 2

N-[1-Phenyl-2-(4-Aminophenyl)ethyl-α-Phenyl-Benzeneacetamide

To a solution of 2-(4-aminophenyl)-1-phenylethylamine (1.0 g, 4.71 mMol), DCC (1.0 g, 4.72 mMol) and DMAP (0.064 g, 0.52 mMol) in dichloromethane (100 mL) was added diphenylacetic acid (1.0 g, 4.72 mMol). The resulting mixture was stirred 18 hours at room temperature. The mixture was filtered and the precipitate was washed with additional dichloromethane. The combined filtrates were concentrated and the resulting crude product was purified by chromatography on silica gel, eluting with 1:1 hexane:ethyl acetate to give 1.37 grams of the title compound.

EXAMPLE 3

N-[1-Phenyl-2-(4-Aminophenyl)ethyl]-α-Phenyl-Benzeneacetamide 2-(4-aminophenyl)-1-phenylethylamine (0.40 g, 1.9 mMol) and diphenylacetic acid (0.40 g, 1.9 mMol) were dissolved in dimethylformamide (DMF) (4 mL) at room temperature. To this was added HOBT (0.26 g, 1.9 mMol), NMM (0.19 g, 1.9 mMol) and EDCl (0.36 g) and the mixture was stirred at room temperature for 18 hours. The DMF was removed under vacuum and the oily residue was taken up in 100 mL ethyl acetate. The ethyl acetate was washed with saturated sodium bicarbonate and with brine, dried over magnesium sulfate, and evaporated to give 0.683 grams of a semi-solid. This was purified on 30 grams of flash-grade silica gel eluting with 100% dichloromethane to give 0.512 grams of the title compound, m.p. 161°–163° C.

Using a similar procedure, the following compounds can be prepared:

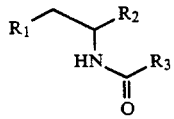

| Compound # | $R_1$ | $R_2$ | $R_3$ | Physical Data |
|---|---|---|---|---|
| 3A | $4-H_2N—C_6H_4—$ | $C_6H_5—$ | $CH_3(CH_2)_{14}—$ | 200MHz NMR(CDCl3)δ= 0.8–0.93(m, 3H); 1.1–1.31(bs, 26H); 1.45–1.64(m, 2H); 2.13(t, 2H, J=8Hz); 2.93(d, 2H, J=7Hz); 3.97(bs, 2H); 5.17(dt, 1H, J=7,7Hz); 5.63(d, 1H, J=7Hz); 6.58(d, 1H, J=7Hz); 6.8(dd, 1H, J=9,2Hz); 7.11–7.36(m, 6H) |
| 3B | $4-H_2N—C_6H_4—$ | $C_6H_5—$ | $CH_3(CH_2)_7CH=CH(CH_2)_7—$ | m.p. 77–80° C. |
| 3C | $4-H_2N—C_6H_4—$ | $C_6H_5—$ | $n-C_9H_{19}—$ | m.p. 105–107° C. |
| 3D | $4-H_2N—C_6H_4—$ | $C_6H_5—$ | $n=C_5H_{11}—$ | m.p. 120–121° C. |
| 3E | $4-H_2N—C_6H_4—$ | $C_6H_5—$ | $n-C_{11}H_{23}$ | m.p. 103–104° C. |
| 3F | $4-H_2N—C_6H_4—$ | $C_6H_5—$ | $4-Cl—C_6H_4—CH(4-Cl—C_6H_4)—$ | m.p. 187–188° C. |
| 3G | $C_6H_5—$ | pyridyl (4-pyridyl) | $CH_3(CH_2)_7CH=CH(CH_2)_7—$ | m.p. 80–83° C. |
| 3H | $3-H_2N—C_6H_4—$ | $C_6H_5—$ | $C_6H_5—CH(C_6H_5)—$ | m.p. 140–144° C. |

-continued

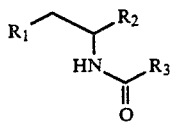

| Compound # | R₁ | R₂ | R₃ | Physical Data |
|---|---|---|---|---|
| 3I | 4-H₂N—C₆H₄— | C₆H₅— | 2-H₃CO, 4-(n-C₁₄H₂₉O)—C₆H₃— | m.p. 109–115° C. |
| 3J | C₆H₅— | 4-pyridyl | C₆H₅—CH(C₆H₅)— | m.p. 145–148° C. |
| 3K | 4-H₂N—C₆H₄— | C₆H₅— | (CH₃)₃COC(O)—NH—(CH₂)₁₀— | m.p. 89–90° C. |
| 3L | 4-H₂N—C₆H₄— | C₆H₅— | (CH₃)₃COC(O)—NH—(CH₂)₁₁— | m.p. 78–82° C. |
| 3M | C₆H₅— | 4-quinolyl | CH₃(CH₂)₇CH=CH(CH₂)₇— | m.p. 121–123° C. |
| 3N | 4-F—C₆H₄— | 4-pyridyl | CH₃(CH₂)₇CH=CH(CH₂)₇— | m.p. 95–97° C. |
| 3O | 3,4-(H₃CO)₂—C₆H₃— | C₆H₅— | C₆H₅—CH(C₆H₅)— | m.p. 166–189° C. |
| 3P | C₆H₅— | 4-quinolyl | C₆H₅—CH(C₆H₅)— | m.p. 184–186° C. |
| 3Q | C₆H₅— | 3-pyridyl | CH₃(CH₂)₇=CH(CH₂)₇— | m.p. 67–69° C. |
| 3R | 4-F—C₆H₄— | 4-pyridyl | C₆H₅—CH(C₆H₅)— | m.p. 196–198° C. |
| 3S | C₆H₅— | 3-pyridyl | C₆H₅—CH(C₆H₅)— | m.p. 152–153° C. |
| 3T | 4-H₂N—C₆H₄— | C₆H₅— | C₆H₅—CH(C₆H₅)— | FAB(M + 1) = 473 |
| 3U | 3-pyridyl | C₆H₅— | CH₃(CH₂)₇CH=CH(CH₂)₇— | m.p. 53–54° C. |
| 3V | 4-pyridyl | C₆H₅ | C₆H₅—CH(C₆H₅)— | m.p. 164–165° C. |

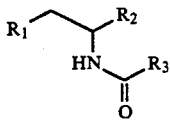

| Compound # | R₁ | R₂ | R₃ | Physical Data |
|---|---|---|---|---|
| 3W | $C_6H_5-$ | $4-H_3CO-C_6H_4-$ | $C_6H_5-CH(C_6H_5)-$ | m.p. 173-174° C. |
| 3X | $C_6H_5-$ | $4-H_3CO-C_6H_4-$ | $CH_3(CH_2)_7CH=CH(CH_2)_7-$ | m.p. 91-93° C. |
| 3Y | $4-H_2N-C_6H_4-$ | $C_6H_5-$ | $C_6H_5-CH(C_6H_5)CH_2-$ | m.p. 161-162° C. |
| 3Z | $4-H_3CO-C_6H_4-$ | $4-H_3CO-C_6H_4-$ | $C_6H_5-CH(C_6H_5)-$ | m.p. 190-193° C. |
| 3AA | $4-H_3CO-C_6H_4-$ | $4-H_3CO-C_6H_4-$ | $CH_3(CH_2)_7CH=CH(CH_2)_7-$ | m.p. 116-118° C. |
| 3BB | $4-H_2N-C_6H_4-$ | $C_6H_5-$ | $C_6H_5-CH_2-CH(C_6H_5)-$ | FAB(M + 1) = 407 |
| 3CC | $C_6H_5-$ | $4-H_2N-C_6H_4-$ | $C_6H_5-CH(C_6H_5)-$ | m.p. 160-162° C. |
| 3DD | $CH_3O_2C-C_6H_4-$ | $C_6H_5-$ | $C_6H_5-CH(C_6H_5)-$ | m.p. 181-183° C. |
| 3EE | pyrazole-N- | $C_6H_5-$ | $C_6H_5-CH(C_6H_5)-$ | m.p. 156-158° C. |
| 3FF | $4-H_3CO-C_6H_4-$m.p. | $C_6H_5-$ | $C_6H_5-CH(C_6H_5)-$ | m.p. 169-171° C. |
| 3GG | SEM-N-imidazole | $C_6H_5-$ | $C_6H_5-CH(C_6H_5)-$ | m.p. 123-123.5° C. |
| 3HH | n-$C_7H_{15}$-N-imidazole | $C_6H_5-$ | $C_6H_5-CH(C_6H_5)-$ | m.p. 116-117° C. |

EXAMPLE 4

α-Phenyl-N-[1-Phenyl-2-(4-Hydroxyphenyl)]-Benzeneacetamide

The product of Example 3FF (66.1 mg, 157 mMol) was treated with boron tribromide (0.32 mMol, 0.32 mL of a 1M solution) in dichloromethane at 0° C. for 1.5 hours. The reaction was quenched with saturated sodium bicarbonate and the reaction mixtures extracted into dichloromethane. The dichloromethane was washed with water and brine, dried over magnesium sulfate, and evaporated. The residue was purified by silica gel chromatography, eluting with 1:1 hexane:ethyl acetate to obtain 53 mg of the title compound. Elemental analysis: calc for $C_{28}H_{25}NO_2$ is C=81.32%, H=6.26%; N=3.39%; Found C=81.28%, H=6.08%, N=3.25%.

EXAMPLE 4A

Using a procedure similar to that of Example 4, treat the product of Example 3W to obtain α-phenyl-N-[1-(4-hydroxyphenyl)-2-phenylethyl]-benzeneacetamide, m.p. 67°-69° C.

EXAMPLE 5

N-[12-[[2-(4-Aminophenyl)-1-Phenylethyl]amino]-12-Oxododecyl]-α-Phenyl-Benzeneacetamide To 1,1-dimethylethyl-12-[[2-(4-aminophenyl)-1-phenylethyl]amino]-12-oxododecylcarbamate (5.2 g, 10.5 mMol) in 80 mL dioxane at 0° C. was added 25 mL saturated HCl in dioxane. The mixture was allowed to come to room temperature while stirring overnight. The solvent was removed under vacuum and the crude product was acylated with diphenyl acetic acid according to the procedure of Example 3 to obtain the title compound, m.p. 107°-114° C.

EXAMPLE 5A

Using a procedure similar to Example 5, treat 1,1-dimethylethyl-11-[[2-(4-aminophenyl)-1-[phenylethyl]amino]-11-oxoundecylcarbamate to obtain N-[11-[[2-(4-aminophenyl)-1-phenylethyl]amino]-11-oxoundecyl]-α-phenyl-benzeneacetamide, m.p. 96°-102° C.

EXAMPLE 6

Treat the product of Example 3A with ICI to obtain N-(1-oxo-hexadecanyl)-1-phenyl-2-(3-iodo-4-aminophenyl)ethyl amine. Elemental analysis: calc for $C_{30}H_{45}IN_2O$ is C=79.95%, H=10.29%, N=6.22%, found C=79.87%, H=10.51%, N=6.34%.

EXAMPLE 7

Carry out a basic hydrolysis of the product of Example 3DD to obtain the corresponding free acid, N-[1-phenyl-2-(4-carboxyphenyl) ethyl]-α-phenyl-benzeneacetamide, m.p. 245°-248° C.

EXAMPLE 8

Treat the product of Example 3 with methanesulfonylchloride to obtain N-[1-phenyl-2-(4-methanesulfonylaminophenyl)ethyl]-α-phenyl-benzeneacetamide, m.p. 200°–202° C.

EXAMPLE 9

Acetylate the product of Example 3 with acetic anhydride/pyridine to obtain N-[1-phenyl-2-(4-acetamidophenyl)ethyl]-α-phenyl-benzeneacetamide, m.p. 247°–249° C.

EXAMPLE 10

(−)
N-[1-Phenyl-2-(4-Aminophenyl)Ethyl]-α-Phenyl-Benzeneacetamide

Using the (−) 2-(4-aminophenyl)-1-phenylethylamine of Preparation 7, follow the procedure of Example 2 to obtain the title compound, $[\alpha]_D^{26} = -1.9°$ C. (MeOH).

Similarly, starting with (+) 2-(4-aminophenyl)-1-phenylethylamine, prepare (+) N-[1-phenyl-2-(4-aminophenyl)ethyl]-α-phenyl-benzeneacetamide, $[\alpha]_D^{26} = +2.1°$ C. (MeOH).

The following formulations exemplify some of the dosage forms of this invention. In each the term "active compound" designates a compound of formula I, preferably (−)-N-[1-phenyl-2-(4-aminophenyl)ethyl]-α-phenyl-benzeneacetamide. However, this compound may be replaced by an equally effective amount of other compounds of formula I.

EXAMPLE A

| No. | Ingredient | Tablets mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried ganules if necessary and mix with Item No. 4 and mix for 10–15 minutes. Add Item No. 5 and mix for 1–3 minutes. Compress the mixture to appropriate size and weight on a suitable tablet machine.

EXAMPLE B

| No. | Ingredient | Capsules mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |

-continued

| No. | Ingredient | Capsules mg/tablet | mg/tablet |
|---|---|---|---|
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

We claim:

1. A compound represented by the formula

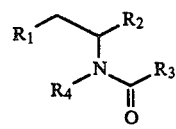

wherein one of $R_1$ and $R_2$ is a heteroaryl group selected from the group consisting of pyridinyl, pyrimidinyl, pyrazinyl, and triazinyl; X-substituted heteroaryl wherein X is 1 to 3 substituents independently selected from the group consisting of halogeno, lower alkyl, hydroxy, lower alkoxy, amino, lower alkylamino, lower dialkylamino, acetamido, methanesulfonylamino, carboxy and lower alkoxycarbonyl; or N-substituted triazinyl wherein the N-substituents are selected from the group consisting of lower alkyl, 2-(trimethylsilyl)ethoxymethyl and $R_5CO$— wherein $R_5$ is lower alkyl, phenyl, benzyl or 2,2-dimethylpropyl;

and the other is phenyl or X-substituted phenyl, wherein X is as defined above;

$R_3$ is a diphenyl substituted alkyl chain of 1 to 25 carbon atoms, branched or straight, saturated or containing one or more double bonds; or —(CH$_2$)$_7$CH=CH(CH$_2$)$_7$CH$_3$;

$R_4$ is hydrogen, lower alkyl, phenyl, or X-substituted phenyl;

or a pharmaceutically acceptable salt thereof.

2. A compound of claim 1 wherein $R_4$ is hydrogen.

3. A compound of claim 2 wherein —C(O)R$_3$ is oleoyl, diphenylacetyl, 2,2-diphenylpropanoyl, or 2,3-diphenylpropanoyl.

4. A compound of claim 3 wherein —C(O)R$_3$ is diphenylacetyl or oleoyl.

5. A compound of claim 1 wherein one of $R_1$ and $R_2$ is heteroaryl and the other is phenyl.

6. A compound of claim 5 wherein one of $R_1$ and $R_2$ is pyridyl.

7. A compound of claim 5 wherein —C(O)R$_3$ is diphenylacetyl or oleoyl.

8. A pharmaceutical composition useful for treating atherosclerosis comprising an ACAT-inhibitory effective amount of a compound of claim 1 in a pharmaceutically effective carrier.

9. A method of treating atherosclerosis comprising administering to a mammal in need of such treatment a pharmaceutical composition of claim 8.

10. A compound of claim 1 represented by the formula:

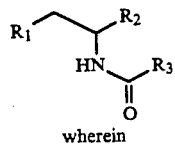
wherein
| Formula | $R_1$ | $R_2$ | $R_3$ |
|---|---|---|---|
| 3G | $C_6H_5-$ | 4-pyridyl | $CH_3(CH_2)_7CH=CH(CH_2)_7-$ |
| 3J | $C_6H_5-$ | 4-pyridyl | $C_6H_5-CH(C_6H_5)-$ |
| 3N | $4-F-C_6H_4-$ | 4-pyridyl | $CH_3(CH_2)_7CH=CH(CH_2)_7-$ |
| 3Q | $C_6H_5-$ | 3-pyridyl | $CH_3(CH_2)_7=CH(CH_2)_7-$ |
| 3R | $4-F-C_6H_4-$ | 4-pyridyl | $C_6H_5-CH(C_6H_5)-$ |
| 3S | $C_6H_5-$ | 3-pyridyl | $C_6H_5-CH(C_6H_5)-$ |
| 3U | 3-pyridyl | $C_6H_5-$ | $CH_3(CH_2)_7CH=CH(CH_2)_7-$ |
| 3V | 4-pyridyl | $C_6H_5$ | $C_6H_5-CH(C_6H_5)-$. |
* * * * *